(12) United States Patent
Wang et al.

(10) Patent No.: US 10,507,225 B2
(45) Date of Patent: Dec. 17, 2019

(54) POWDER FOR REGULATING INTESTINAL FLORA AND PROTECTING GASTRIC MUCOSA, PREPARATION METHOD AND USE THEREOF

(71) Applicant: INFINITUS (CHINA) COMPANY LTD., Jiang Men, Guangdong (CN)

(72) Inventors: Lei Wang, Guangdong (CN); Ruiqi He, Guangdong (CN); Hongwei Zhao, Guangdong (CN); Qingtao Tang, Guangdong (CN)

(73) Assignee: INFINITUS (CHINA) COMPANY LTD., Jiang Men, Guangdong (CN)

( * ) Notice: Subject to any disclaimer, the term of this patent is extended or adjusted under 35 U.S.C. 154(b) by 0 days.

(21) Appl. No.: 15/956,518

(22) Filed: Apr. 18, 2018

(65) Prior Publication Data

US 2019/0125820 A1 May 2, 2019

(30) Foreign Application Priority Data

Oct. 26, 2017 (CN) .......................... 2017 1 1014683

(51) Int. Cl.
| | | |
|---|---|---|
| *A61K 36/9064* | (2006.01) | |
| *A61K 9/16* | (2006.01) | |
| *A61K 36/344* | (2006.01) | |
| *A61K 36/284* | (2006.01) | |
| *A61K 36/8945* | (2006.01) | |
| *A61K 36/076* | (2006.01) | |
| *A61K 36/48* | (2006.01) | |
| *A61K 36/752* | (2006.01) | |
| *A61K 36/07* | (2006.01) | |

(52) U.S. Cl.
CPC ........ *A61K 36/9064* (2013.01); *A61K 9/1623* (2013.01); *A61K 9/1652* (2013.01); *A61K 36/07* (2013.01); *A61K 36/076* (2013.01); *A61K 36/284* (2013.01); *A61K 36/344* (2013.01); *A61K 36/48* (2013.01); *A61K 36/752* (2013.01); *A61K 36/8945* (2013.01)

(58) Field of Classification Search
None
See application file for complete search history.

(56) References Cited

U.S. PATENT DOCUMENTS

| 6,592,863 B2 * | 7/2003 | Fuchs ................... A23K 50/40 424/93.1 |
| 9,084,434 B2 * | 7/2015 | Hodal, Jr. ............ A61K 9/2018 |

OTHER PUBLICATIONS

The 1st Office Action for a Taiwanese Patent application No. 107105060, dated Jun. 28, 2018.
Infinitus Gest-Aid Plus, Product serial No. 13047001, Aug. 5, 2014.
Li Yulu & Liu Liping, "The Characteristics of Inulin and Its Application in Food Industry", College of Chemistry and Food Safety, Bohai University, Jinzhou, Liaoning 121000, May 5, 2014.

* cited by examiner

Primary Examiner — Susan Hoffman
(74) Attorney, Agent, or Firm — Yue(Robert) Xu; Apex Attorneys at Law, LLP

(57) ABSTRACT

The present disclosure relates to the field of health care products. The present disclosure provides a powder which is prepared from xylooligosaccharide, isomaltooligosaccharide, mannitol, inulin, RADIX CODONOPSIS, FRUIT BODY HERICIUM ERINACEUS extract, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA. All raw materials are from natural Chinese herbal medicine. No additives are added. The method for preparing the powder in the present disclosure is simple and suitable for large-scale production. Also, it is easy to be carried. Experiment data shows that the powder described in the present disclosure has the function of relieving the gastric mucosal injury by reducing the acute gastric mucosal injury induced by ethanol effectively and has the function of regulating gastric mucosa. Therefore, the powder could be used to prepare the health care product which has the function of regulating gastrointestinal tract and protecting the gastric mucosa.

1 Claim, No Drawings

POWDER FOR REGULATING INTESTINAL FLORA AND PROTECTING GASTRIC MUCOSA, PREPARATION METHOD AND USE THEREOF

CROSS REFERENCE TO RELATED APPLICATIONS

This application claims the priority of Chinese Patent Application No. 201711014683.6, filed on Oct. 26, 2017, and titled with "POWDER FOR REGULATING INTESTINAL FLORA AND PROTECTING GASTRIC MUCOSA, PREPARATION METHOD AND USE THEREOF", and the disclosures of which are hereby incorporated by reference.

FIELD

The present invention relates to the field of health care products, specifically to a powder having functions of regulating intestinal flora and protecting gastric mucosa, and a preparation method thereof; in particular, the present invention relates to a powder having functions of regulating intestinal flora and protecting gastric mucosa prepared by using natural Chinese herbal medicine as the main raw material and a preparation method thereof.

BACKGROUND

Gastrointestinal tract is the main organ of the human digestive system, generally referring to the stomach, duodenum, small intestine, large intestine and rectum. The functions of gastrointestinal tract mainly include digestion, absorption and excretion. Digestion requires a combinatory effect including biochemical effect of gastric acid, different kinds of digestive juice and digestive enzymes, mechanical physical gastrointestinal movement and the physiological effect of normal intestinal flora. Absorption is achieved mainly through the gastrointestinal mucosa cells. Excretion is the function of the rectum and sphincter. It requires not only good food hygiene, eating habits, and dining environment, but also timely prevention and treatment of gastrointestinal diseases, such as indigestion, ulceration, diarrhea, constipation and hemorrhoids, to maintain good gastrointestinal function.

With the accelerating pace of modern life, continuously increasing work pressure, increasingly irregular eating and sleeping behaviors, people's gastrointestinal function is also deteriorating, with frequent appearance of symptoms such as hiccups, dry mouth, mouth pain, chest tightness, sour regurgitation, anorexia, nausea, vomiting, fullness after eating less, abdominal pain, bloating, diarrhea or constipation, and the subsequent appearance of fatigue, weakness, drowsiness and lack of concentration etc., leaving one in a constant sub-health status, which produces serious effects on people's daily life, work and study.

In recent years, people's living standard has been obviously improved, which leads to a great change to people's concepts of consumption and health. In order to avoid the adverse effects of unhealthy states, people are paying more and more attention to the use of nutrition and health care products. At present, most of the health care products for improving the gastrointestinal function take the form of oral liquid, focusing on the effects of regulating the beneficial intestinal flora, relieving constipation and repairing gastric mucosa etc. Oral liquid has the disadvantages of inconvenience of taking, poor stability and short storage time. The preparation of tablets requires addition of large doses of excipients, such as starches and hydroxymethyl cellulose, which makes tablet have a long disintegration time and inconvenience of taking for people with difficulty in swallowing, such as the elder and the children.

SUMMARY

In view of the above, the purpose of the present disclosure is to provide a powder with functions of regulating intestinal flora and protecting gastric mucosa and preparation method thereof, against the defects in the prior art. The health care product powder of the present disclosure is mainly made from natural Chinese herbal medicine and has the function of regulating intestinal flora and protecting the gastric mucosa. Also, no excipient such as starches and hydroxymethyl cellulose is added, which has no negative effects on the dissolution of effective ingredients and bioavailability and keeps the powder in good conditions.

In order to achieve the purpose of the present disclosure, the present invention adopts the following technical solutions:

A powder having the function of regulating intestinal flora and protecting the gastric mucosa, which is prepared from inulin, xylooligosaccharide, isomaltooligosaccharide, mannitol, RADIX CODONOPSIS, FRUIT BODY HERICIUM ERINACEUS extract, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA.

Preferably, the mass ratio of inulin, xylooligosaccharide, isomaltooligosaccharide, mannitol, RADIX CODONOPSIS, FRUIT BODY HERICIUM ERINACEUS extract, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA is (10~30):(10~30):(10~20):(10~20):(3~10):(3~10):(3~8):(3~8):(2~5):(2~5):(1~5):(1~5).

In some embodiments, the mass ratio of inulin, xylooligosaccharide, isomaltooligosaccharide, mannitol, RADIX CODONOPSIS, FRUIT BODY HERICIUM ERINACEUS extract, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA is 10:20:10:10:5:10:5:8:3:5:2:2.

In some embodiments, the mass ratio of inulin, xylooligosaccharide, isomaltooligosaccharide, mannitol, RADIX CODONOPSIS, FRUIT BODY HERICIUM ERINACEUS extract, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA is 20:10:20:20:4:4:4:4:3:3:3:3.

In other embodiments, the mass ratio of inulin, xylooligosaccharides, isomaltooligosaccharide, mannitol, RADIX CODONOPSIS, FRUIT BODY HERICIUM ERINACEUS extract, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA is 20:15:14:10:7.5:7.5:7.5:6:5:5:3.5:3.5.

The present disclosure further provides a preparation method for the powder, comprising: extracting RADIX CODONOPSIS, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA with water; collecting the extraction solution; adding inulin, xylooligosaccharide, isomaltooligosaccharide and FRUIT BODY HERICIUM ERINACEUS extract to the extraction solution and mixing; drying and pulverizing the mixture.

Wherein the water extracting is the extract through decoction with water.

Further, the decoction is preferably performed 1~2 times with 3~20 times of water for 0.5~4 h every time.

In some embodiments, the decoction is performed with 20 times of water for 3 h.

In some embodiments, the decoction is performed with a first extraction with 5~20 times of water for 0.5~3 h and a second extraction with 3~15 times of water for 0.5~2 h. In some embodiments, the first extraction is performed with 15 times of water for 2 h and the second extraction is performed with 10 times of water for 1 h. In other embodiments, the first extraction is performed with 5 times of water for 1 h and the second extraction is performed with 5 times of water for 0.5 h.

The preparation method described in the present disclosure comprises the steps of collecting the extraction liquid after water extraction and concentrating the extraction liquid, preferably vacuum concentration.

Furthermore, the preparation method described in the present disclosure comprises the step of drying by adding inulin after concentration; spray drying, freeze drying, belt drying, microwave drying or vacuum drying is preferred.

The particle size of pulverization of the preparation method described in the present invention is preferably kept from 40 to 80 meshes.

In a particular embodiment, the powder is administered by gavage in the present disclosure and the effect of the powder on the gastric mucosal injury is observed. The result shows that the powder described in the present disclosure ameliorates the gastric mucosal injury and reduces the acute gastric mucosal injury induced by absolute ethanol.

In a particular embodiment, the powder is administered by gavage in the present disclosure and the effect of the powder on the gastric mucosa is observed. The result shows that the powder described in the present disclosure ameliorates the gastric mucosal injury and reduces the acute gastric mucosal injury induced by ethanol.

Therefore, the present disclosure provides the application of the powder for the preparation of health care food which has the functions of regulating intestinal flora and protecting the gastric mucosa.

As seen from the above technical solution, the present disclosure provides a powder prepared from xylooligosaccharide, isomaltooligosaccharide, mannitol, inulin, RADIX CODONOPSIS, FRUIT BODY HERICIUM ERINACEUS extract, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA. The raw materials are all derived from natural Chinese herbal medicine. No additives are added. The ingredients are natural and clean. It conforms to people's trend of pursuing the natural and healthy food, with the advantages of small taking dosage, convenient taking, which can be orally taken directly or dissolved in water, good solubility in cold water, good taste and fast absorption. The preparation method of the powder described in the present disclosure is simple, which is suitable for large-scale production and easy to be carried. The powder prepared has good stability and long storage time. Experiment data shows that the powder described in the present disclosure has the function of relieving the gastric mucosal injury by reducing the acute gastric mucosal injury induced by ethanol effectively and has the function of regulating gastric mucosa.

Therefore, the powder can be used to prepare the health care product which has the function of regulating gastrointestinal tract and protecting the gastric mucosa.

DETAILED DESCRIPTION

The present disclosure discloses a powder with the functions of regulating intestinal flora and protecting gastric mucosa, a preparation method and application thereof. Those skilled in the art can learn from the contents of the disclosure, and properly improve the process parameters. It is specifically to be noted that all similar substitutions and modifications will be apparent to those skilled in the art and considered as included in the present invention. The method and product described in the present disclosure have been described with reference to the preferred embodiments. It will be apparent to those skilled in the art that various changes, modifications and combinations may be made to the methods described herein without departing from the spirit, scope and spirit of the invention, to implement the present invention.

For further understanding of the present invention, the technical solutions in the embodiments of the present invention will be described clearly and completely below with reference to the embodiments of the present invention. Apparently, the described embodiments are only a part but not all of the embodiments of the present invention. All other embodiments obtained by those skilled in the art based on the embodiments of the present invention without creative efforts shall fall within the protection scope of the present invention.

Unless otherwise specified, the reagents involved in the examples of the present invention are all commercially available in the market. FRUIT BODY HERICIUM ERINACEUS extract are prepared from FRUIT BODY HERICIUM ERINACEUS by water extraction and alcohol precipitation, with the content of FRUIT BODY HERICIUM ERINACEUS extract higher than 15%.

Example 1. Powder of the Present Disclosure

Formula

| | |
|---|---|
| Xylooligosaccharide | 10 g |
| Isomaltooligosaccharide | 20 g |
| Mannitol | 10 g |
| Inulin | 10 g |
| RADIX CODONOPSIS | 5 g |
| FRUIT BODY HERICIUM ERINACEUS extract | 10 g |
| RHIZOMA DIOSCOREA OPPOSITA | 5 g |
| SCLEROTIUM PORIA | 8 g |
| SEMEN DOLICHOS | 3 g |
| PERICARPIUM CITRUS | 5 g |
| FRUCTUS AMOMUM | 2 g |
| RHIZOMA MACROCEPHALA | 5 g |

Preparation method: RADIX CODONOPSIS, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA were decocted with water twice, with 13 times of water for 3 h at the first time, and 15 times of water for 3.5 h at the second time. The two extraction solutions were combined and then subjected to vacuum concentration. Inulin, FRUIT BODY HERICIUM ERINACEUS extract, xylooligosaccharide, isomaltooligosaccharide and mannitol were added into the concentrated solution, which was then subjected to spray drying to obtain a Chinese herbal medicine extract powder, with a particle size of 40 to 80 meshes.

Example 2. Health Care Powder of the Present Disclosure

Formula

| | |
|---|---|
| Xylooligosaccharide | 20 g |
| Isomaltooligosaccharide | 10 g |
| Mannitol | 20 g |
| Inulin | 20 g |
| RADIX CODONOPSIS | 4 g |
| FRUIT BODY HERICIUM ERINACEUS extract | 4 g |
| RHIZOMA DIOSCOREA OPPOSITA | 4 g |
| SCLEROTIUM PORIA | 4 g |
| SEMEN DOLICHOS | 3 g |
| PERICARPIUM CITRUS | 3 g |
| FRUCTUS AMOMUM | 3 g |
| RHIZOMA MACROCEPHALA | 3 g |

Preparation method: RADIX CODONOPSIS, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA were decocted with water twice, with 12 times of water for 2.5 h at the first time, and 14 times of water for 3.5 h at the second time. The two extraction solutions were combined and then subjected to vacuum concentration. Inulin, FRUIT BODY HERICIUM ERINACEUS extract, xylooligosaccharide, isomaltooligosaccharide and mannitol were added into the concentrated solution, which was then subjected to spray drying to obtain a Chinese herbal medicine extract powder, with a particle size of 40 to 80 meshes.

Example 3. Health Care Powder of the Present Disclosure

Formula

| | |
|---|---|
| Xylooligosaccharides | 20 g |
| Isomaltooligosaccharide | 15 g |
| Mannitol | 14 g |
| Inulin | 10 g |
| RADIX CODONOPSIS | 7.5 g |
| FRUIT BODY HERICIUM ERINACEUS extract | 7.5 g |
| RHIZOMA DIOSCOREA OPPOSITA | 7.5 g |
| SCLEROTIUM PORIA | 6 g |
| SEMEN DOLICHOS | 5 g |
| PERICARPIUM CITRUS | 5 g |
| FRUCTUS AMOMUM | 3.5 g |
| RHIZOMA MACROCEPHALA | 3.5 g |

Preparation method: RADIX CODONOPSIS, RHIZOMA DIOSCOREA OPPOSITA, SCLEROTIUM PORIA, SEMEN DOLICHOS, PERICARPIUM CITRUS, FRUCTUS AMOMUM and RHIZOMA MACROCEPHALA were decocted with water twice, with 13 times of water for 2.5 h at the first time, and 14 times of water for 3.5 h at the second time. The two extraction solutions were combined and then subjected to vacuum concentration. Inulin, FRUIT BODY HERICIUM ERINACEUS extract, xylooligosaccharide, isomaltooligosaccharide and mannitol were added into the concentrated solution, which was then subjected to spray drying to obtain a Chinese herbal medicine extract powder, with a particle size of 40 to 80 meshes.

Experimental Example 1. Auxiliary Protection Effect for Gastric Mucosa Injury 1. Test sample: the powder prepared in Example 2.
2. Test animals: SD rat, male, 160-180 g.
3. Grouping and the duration time of administration of the test sample:

Test animals were divided into 5 groups, i.e., a model group, a blank group, low dosage group, medium dosage group and high dosage group, wherein the dosage groups were set at 5 times (166.67 mg/kg), 10 times (333.33 mg/kg) and 30 times (1000 mg/kg) of the human recommended amount, respectively. The test samples were applied for 4 weeks.

4. Test indexes: gastric mucosal injury, pathological damage of gastric mucosa and scores.
5. Results:

5.1. Analysis of acute gastric mucosal injury

After 1 h of absolute ethanol injury, the stomach of each rat was dissected. The gastric mucosa of the blank group was found to be smooth and intact without any bleeding, while the remaining groups of rats showed mucosal bleeding and tissue necrosis. The animals in the model group had the most severe injuries, manifested as massive congestion in bright red color. The animals in the high, medium and low dosage groups showed punctate or strip-shaped bleeding, and the bleeding area was significantly reduced. According to the grading standards, the injury scores of each group were shown in Table 1. The powder reduced the gastric mucosal injury induced by absolute ethanol in a dose-dependent manner.

TABLE 1

Scores of the Gastric Mucosa Injuries in Each Group

| Group | Blank group | Model group | Low dosage group | Medium dosage group | High dosage group |
|---|---|---|---|---|---|
| Injury incidence | — | 100% | 100% | 100% | 100% |
| Injury index | — | 9.00 | 5.67 | 5.14 | 4.38 |
| Injury inhibition rate | — | — | 37.00% | 42.95% | 51.3% |

5.2 Histological Results

The results of pathological examination were consistent with the gross findings of the naked eye, and the gastric mucosal injury in the model group was the most serious. Each treatment group showed a protection effect on gastric mucosal injury in a dose-dependent manner.

6. Conclusion (1) Observation index: Except for the rats in the blank group, the incidence of gastric mucosal injury in each group was 100%. The injury inhibition rate was 37% in the low dosage group, 42.9% in the medium dosage group and 51.3% in the high dosage group, indicating that the protective effect of the product for the gastric mucosal injury was dose-dependent.

(2) Pathological observation and score: It was found that the protective effect for gastric mucosal injury of each dosage group was significant by calculating the injury inhibition rate through the bleeding spot and the pathological analysis. The acute gastric mucosal injury induced by absolute ethanol was reduced effectively in a dose-dependent manner.

The powder prepared in Example 1 and Example 3 was tested according to the above method and the results were equivalent to those of Example 2.

Experimental Example 2. Effect of Regulating the Intestinal Flora

1. Test sample: the powder prepared in Example 2.
2. Test animals: Balb/C mice, male, 18-22 g.
3. Grouping and the Duration Time of Administration of the Test Sample:

Test animals were divided into 4 groups, i.e. a blank group, low dosage group, medium dosage group and high dosage group, wherein the dosage groups were set at 5 times (166.67 mg/kg), 10 times (333.33 mg/kg) and 20 times (666.66 mg/kg) of the human recommended amount, respectively. The test samples were applied for 4 weeks.

4. Observation indexes: weight, *Bifidobacterium, Lactobacillus, Enterococcus, Enterobacter, Clostridium, Fusobacterium* and *Bacteroides*.
5. Test method:

Prior to the administration of the test sample, 0.1 g of mouse feces was aseptically collected and diluted at 10 times serial concentration, and the appropriate dilutions were inoculated on corresponding medium. After culturing, colonies were counted with reference to colony morphology, Gram staining under microscopy, and biochemical reaction, etc. to calculate the colony number per gram of wet stool.

After statistical analysis through taking the logarithm, the property of the intestinal flora was determined. The test samples were then applied to the mice respectively, with normal feed and water for 14 days. 24 hours after the last administration of the test sample, rectal stool was collected in the same manner and the intestinal flora was detected as above. The changes of *Bifidobacterium, Lactobacillus, Enterococcus, Enterobacter, Clostridium, Fusobacterium* and *Bacteroides* before and after the experiment and between the groups were compared.

6. Data processing:

T-test of two independent samples was employed for the significance test of difference between two groups, and one-way ANOVA significance test was used to compare the mean of multiple groups.

7. Results and analysis 7.1 Clinical manifestation and weigh growth curve

After 4 weeks of administration, the mice in blank group have loose skin and reduced activity. Compared with the blank group, the mice in each dosage group have bright, shiny fur and showed an active performance.

As shown in Table 2, the weight of the animals in blank group decreased in the last week, probably due to the physiological aging and growth arrest caused by prolonged administration. Weigh of the animals in each dosage group increased, showing statistical difference among low dosage group, high dosage group and normal group.

TABLE 2

| Weight change of mice | | | | | | | | | | | | | |
|---|---|---|---|---|---|---|---|---|---|---|---|---|---|
| Group | Week | 1 | 2 | 3 | 4 | 5 | 6 | 7 | 8 | 9 | 10 | Average weight | SD |
| Blank | 4 | 27.1 | 29.5 | 27.3 | 25.7 | 26.1 | 24.4 | 26.8 | 23.7 | 24.9 | 25.5 | 26.1 | 1.67 |
| Low dosage | 4 | 27.5 | 30.9 | 32.8 | 30.8 | 31.8 | 30.9 | 30.1 | 32.3 | 25.4 | 31 | 30.4* | 2.26 |
| Medium dosage | 4 | 25.3 | 25.6 | 25.9 | 27.4 | 27.5 | 28.7 | 26.7 | 27.2 | 22.6 | 28.8 | 26.6 | 1.83 |
| High dosage | 4 | 31.8 | 27.2 | 27.2 | 29.4 | 28.5 | 23.7 | 29.5 | 31.1 | 29.7 | 25.9 | 28.4* | 2.45 |

*$P < 0.05$, compared with blank group.

7.2 Analysis of intestinal flora changes

After 3 weeks of administration, except there was no significant difference in the number of *Enterobacter* among the groups, all the other strains showed an increase or decrease. Compared with the blank group, the number of the probiotics *Bifidobacterium* (in low and medium dosage groups), *Lactobacillus* (in high dosage group) and *Bacteroides* (in medium and high dosage groups) were increased (Table 3-7). However, the number of non-probiotics *Enterococcus* (in medium and high dosage groups) showed a significant decrease, while the number of *Fusobacterium* (in low and high dosage groups) and *Clostridium* (low dosage group) decreased slightly. The above results show that the product has a good regulatory effect on intestinal flora.

TABLE 3

| Counting results of intestinal flora in blank group | | | | | | | |
|---|---|---|---|---|---|---|---|
| Blank group | CK-1 | CK-2 | CK-3 | CK-4 | CK-5 | CK-6 | Avergage ± SD |
| *Bifidobacterium* *10^6 | 68 | 80.5 | 98 | 68.5 | 81 | 83.5 | 79.9 ± 11.1 |
| *Lactobacillus* *10^6 | 13.1 | 2.2 | 41 | 19.2 | 22.3 | 40.5 | 23.1 ± 15.3 |
| *Enterobacter* *10^4 | 15 | 10 | 16 | 6 | 33 | 40 | 20 ± 13.5 |
| *Enterococcus* *10^6 | 30 | 21.6 | 78 | 54.5 | 46 | 42.5 | 45.4 ± 19.8 |
| *Fusobacterium* *10^6 | 63.5 | 48 | 83 | 57 | 76 | 70.5 | 66.3 ± 12.8 |
| *Clostridium* *10^6 | 28.5 | 25.5 | 14.1 | 21 | 23.2 | 29.6 | 23.7 ± 5.7 |
| *Bacteroides* *10^5 | 25 | 18 | 23 | 13.5 | 11.6 | 11.3 | 17.1 ± 5.91 |

TABLE 4

Counting results of intestinal flora in low dosage group

| Low dosage group | CK-1 | CK-2 | CK-3 | CK-4 | CK-5 | CK-6 | Average ± SD |
|---|---|---|---|---|---|---|---|
| Bifidobacterium *10^6 | 135 | 188 | 93.5 | 98.5 | 98.5 | 105 | 119.7 ± 36.6* |
| Lactobacillus *10^6 | 17.2 | 18.2 | 25.5 | 45 | 19.5 | 12.3 | 22.9 ± 11.6 |
| Enterobacter *10^4 | 10.5 | 17 | 23 | 22 | 20.5 | 20.5 | 18.9 ± 4.6 |
| Enterococcus *10^6 | 44.5 | 43.2 | 41 | 56.5 | 36 | 29.3 | 41.8 ± 9.12 |
| Fusobacterium *10^6 | 40.5 | 21.5 | 36.3 | 37.5 | 37 | 53.5 | 37.7 ± 10.2* |
| Clostridium *10^6 | 13.7 | 5.2 | 16.6 | 14 | 13.7 | 11.9 | 12.5 ± 3.9* |
| Bacteroides *10^5 | 21 | 19 | 19 | 21 | 12.6 | 13.7 | 17.7 ± 3.6 |

Note:
*$P < 0.05$, compared with blank group.

TABLE 5

Counting results of intestinal flora in medium dosage group

| Medium dosage group | CK-1 | CK-2 | CK-3 | CK-4 | CK-5 | CK-6 | Average ± SD |
|---|---|---|---|---|---|---|---|
| Bifidobacterium *10^6 | 198 | 184.5 | 142.5 | 117.5 | 189 | 147.5 | 163.2 ± 31.9* |
| Lactobacillus *10^6 | 32 | 28 | 26.35 | 32 | 19.2 | 14.2 | 25.3 ± 7.19 |
| Enterobacter *10^4 | 17.9 | 18.3 | 12 | 17 | 22 | 19.5 | 17.8 ± 3.3 |
| Enterococcus *10^6 | 29.2 | 26.5 | 15.3 | 15.5 | 17.5 | 18.8 | 20.5 ± 5.9* |
| Fusobacterium *10^6 | 57.5 | 69.5 | 76.5 | 54 | 73 | 61 | 65.3 ± 9.0 |
| Clostridium *10^6 | 26.9 | 20.4 | 23.9 | 22.9 | 22.3 | 28.3 | 24.1 ± 3.0 |
| Bacteroides *10^5 | 22 | 26.5 | 29.5 | 34.5 | 30 | 26 | 28.1 ± 4.3* |

Note:
*$P < 0.05$, compared with blank group.

TABLE 6

Counting results of intestinal flora in high dosage group

| High dosage group | CK-1 | CK-2 | CK-3 | CK-4 | CK-5 | CK-6 | Average ± SD |
|---|---|---|---|---|---|---|---|
| Bifidobacterium *10^6 | 112 | 125 | 81.5 | 80.5 | 145.5 | 86.5 | 105.2 ± 26.8 |
| Lactobacillus *10^6 | 33 | 26 | 35 | 50 | 52.5 | 37.5 | 39.3 ± 10.3* |
| Enterobacter *10^4 | 16.5 | 25 | 15.5 | 10 | 17.5 | 13.5 | 16.3 ± 5 |
| Enterococcus *10^6 | 31 | 25 | 17.1 | 29.7 | 30.5 | 25.7 | 26.5 ± 5.3* |
| Fusobacterium *10^6 | 44.9 | 54 | 41.5 | 54.5 | 57 | 58.5 | 51.7 ± 6.9* |
| Clostridium *10^6 | 30.7 | 26.5 | 19.3 | 29.0 | 19.3 | 22.9 | 24.6 ± 4.9 |
| Bacteroides *10^5 | 55 | 48.5 | 42 | 51 | 55.5 | 38.5 | 48.4 ± 6.9* |

Note:
*$P < 0.05$, compared with blank group.

TABLE 7

Comparison of the intestinal flora change among the groups

| | Folds relative to the control group | | | |
|---|---|---|---|---|
| Species | Blank group | Low dosage | Medium dosage | High dosage |
| Bifidobacterium *10^6 | 1 | 1.5* | 2.04* | 1.32 |
| Lactobacillus *10^6 | 1 | 0.99 | 1.1 | 1.7* |
| Enterobacter *10^4 | 1 | 0.94 | 0.89 | 0.82 |
| Enterococcus *10^6 | 1 | 0.99 | 0.45* | 0.58* |
| Fusobacterium *10^6 | 1 | 0.57* | 0.98 | 0.76* |
| Clostridium *10^6 | 1 | 0.53* | 1.02 | 1.04 |
| Bacteroides *10^5 | 1 | 1.04 | 1.65* | 2.84* |

Note:
*$P < 0.05$, compared with blank group.

8. Conclusion

The status of weigh increase: After 4 weeks of administration, the body weight of blank group decreased in the last week, possibly due to the growth stagnation resulted from the prolonged administration. The body weight of mice in all the dosage groups increased, wherein the low and high dose groups showed statistical differences compared with the blank group.

After 3 weeks of administration, except there was no significant difference in the number of Enterobacter among the groups, the numbers of all the other strains showed an increase or decrease. Compared with the blank group, the probiotics Bifidobacterium (in low and medium dosage groups), Lactobacillus (in high dosage group) and Bacteroides (in medium and high dosage groups) were increased. However, non-probiotics Enterococcus (in middle and high dosage groups) showed significant decrease, while Fusobacterium (in low and high dosage groups) and Clostridium (in low dosage group) decreased slightly. The above results show that the product has a good regulatory effect on intestinal flora.

The powder prepared in Example 1 and Example 3 was tested according to the above method, and the results were equivalent to those of Example 2.

What is claimed is:

1. A method for regulating intestinal flora and protecting gastric mucosa, comprising administering an effective amount of a powder to a subject in need thereof,
wherein the powder is consisted of xylooligosaccharide, isomaltooligosaccharide, mannitol, inulin, RADIX CODONOPSIS, FRUIT BODY HERICIUM ERINACEUS extract, RHIZOMA DIOSCOREA OPPOSITA, SCLEROTIUM PORIA, SEMEN DOLICHOS, PERICARPIUM CITRUS, FRUCTUS AMOMUM and RHIZOMA ATRACTYLODIS MACROCEPHALAE,
wherein the mass ratio of inulin, xylooligosaccharide, isomaltooligosaccharide, mannitol, RADIX CODONOPSIS, FRUIT BODY HERICIUM ERINACEUS extract, RHIZOMA DIOSCOREAa OPPOSITA, SCLEROTIUM PORIA, SEMEN DOLICHOS, PERICARPIUM CITRUS, FRUCTUS AMOMUM and RHIZOMA ATRACTYLODIS MACROCEPHALAE is 20:10:20:20:4:4:4:4:3:3:3:3.

* * * * *